(12) United States Patent
Teixeira et al.

(10) Patent No.: US 11,410,374 B2
(45) Date of Patent: Aug. 9, 2022

(54) SYNTHETIC PARAMETERIZED COMPUTED TOMOGRAPHY FROM SURFACE DATA IN MEDICAL IMAGING

(71) Applicant: Siemens Healthcare GmbH, Erlangen (DE)

(72) Inventors: Brian Teixeira, Lawrence Township, NJ (US); Vivek Kumar Singh, Princeton, NJ (US); Birgi Tamersoy, Erlangen (DE); Andreas Krauß, Bubenreuth (DE); Yifan Wu, Philadelphia, PA (US)

(73) Assignee: Siemens Healthcare GmbH, Erlangen (DE)

( * ) Notice: Subject to any disclaimer, the term of this patent is extended or adjusted under 35 U.S.C. 154(b) by 109 days.

(21) Appl. No.: 16/597,035

(22) Filed: Oct. 9, 2019

(65) Prior Publication Data

US 2021/0110594 A1    Apr. 15, 2021

(51) Int. Cl.
| | |
|---|---|
| G06K 9/00 | (2022.01) |
| G06T 15/08 | (2011.01) |
| G06T 7/50 | (2017.01) |
| G06T 7/11 | (2017.01) |
| A61B 5/00 | (2006.01) |
| A61B 6/03 | (2006.01) |
| G06N 3/08 | (2006.01) |

(52) U.S. Cl.
CPC ............ *G06T 15/08* (2013.01); *A61B 5/0073* (2013.01); *A61B 6/032* (2013.01); *G06N 3/08* (2013.01); *G06T 7/11* (2017.01); *G06T 7/50* (2017.01); *G06T 2207/10081* (2013.01); *G06T 2207/20081* (2013.01); *G06T 2207/20084* (2013.01); *G06T 2207/30004* (2013.01)

(58) Field of Classification Search
None
See application file for complete search history.

(56) References Cited

U.S. PATENT DOCUMENTS

| | | | |
|---|---|---|---|
| 10,849,585 | B1 | 12/2020 | Teixeira et al. |
| 2018/0228450 | A1 | 8/2018 | Vega et al. |
| 2018/0228460 | A1* | 8/2018 | Singh ................. A61B 6/545 |
| 2019/0057521 | A1 | 2/2019 | Teixeira |
| 2019/0214135 | A1 | 7/2019 | Wu |
| 2019/0223819 | A1 | 7/2019 | Mansi et al. |

(Continued)

OTHER PUBLICATIONS

Wu, Yifan, et al. "Towards Generating Personalized Volumetric Phantom from Patient's Surface Geometry." International Conference on Medical Image Computing and Computer-Assisted Intervention. Springer, Cham, 2018.

(Continued)

*Primary Examiner* — Wei Wen Yang

(57) ABSTRACT

Synthetic CT is estimated for planning or other purposes from surface data (e.g., depth camera information). The estimation uses parameterization, such as landmark and/or segmentation information, in addition to the surface data. In training and/or application, the parameterization may be used to correct the predicted CT volume. The CT volume may be predicted as a sub-part of the patient, such as estimating the CT volume for scanning one system, organ, or type of tissue separately from other system, organ, or type of tissue.

17 Claims, 3 Drawing Sheets

(56) References Cited

U.S. PATENT DOCUMENTS

2020/0375546 A1    12/2020  Shoudy et al.

OTHER PUBLICATIONS

McCollough, Cynthia H., et al. "Strategies for reducing radiation dose in CT." Radiologic Clinics 47.1 (2009): 27-40.
Teixeira, Brian, et al. "Generating Synthetic X-ray Images of a Person from the Surface Geometry." Proceedings of the IEEE Conference on Computer Vision and Pattern Recognition. 2018.
Zacharias, Claudia, et al. "Pediatric CT: strategies to lower radiation dose." American Journal of Roentgenology 200.5 (2013): 950-956.

* cited by examiner

SYNTHETIC PARAMETERIZED COMPUTED TOMOGRAPHY FROM SURFACE DATA IN MEDICAL IMAGING

BACKGROUND

The present embodiments relate to estimating three-dimensional computed tomography (CT) for medical imaging. CT plays a pivotal role in clinical diagnosis and therapy planning. However, acquisition of CT data exposes patients to potentially harmful ionizing radiation. Existing CT scan planning is often performed based on coarse patient measurement estimates from visual inspection by the technician or using scouting scans (e.g., a two-dimensional (2D) topogram). For certain other imaging methods, such as emission-based tomography (PET/SPECT), a CT scan is obtained prior to the procedure, to be used for attenuation correction. Both these methods expose patients to additional radiation.

Radiation exposure may be reduced by tube current modulation, automatic exposure control, or adjusting the kV based on patient size. While these approaches reduce the radiation dose, they still require visual inspection by the technician or the use of scouting scans (e.g., scan to acquire a 2D topogram). To avoid ionizing radiation, a phantom topogram of the patient may be predicted from surface data. While this non-ionizing approach is a good approach for replacing scouting scans, the 2D representation of the internal anatomy may lack information for specific planning. Synthetic CT may be generated from the surface geometry, but this approach is only constrained on the surface data.

SUMMARY

Systems, methods, and instructions on computer readable media are provided for CT prediction from surface data. Synthetic CT is estimated for planning or other purposes from surface data (e.g., depth camera information). The estimation uses parameterization, such as landmark and/or segmentation information, in addition to the surface data. In training and/or application, the parameterization may be used to correct the predicted CT volume. The CT volume may be predicted as a sub-part of the patient, such as estimating the CT volume for scanning one system, organ, or type of tissue separately from other system, organ, or type of tissue.

In a first aspect, a method is provided for computed tomography (CT) prediction from surface data in a medical imaging system. A sensor captures an outer surface of a patient. A segmentation and/or a landmark location are determined. An image processor generates a first three-dimensional (3D) CT representation of the patient by a first machine-learned generative network in response to input of the surface data and the segmentation and/or landmark location to the first machine-learned generative network. The surface data is from an output of the sensor for the outer surface. A display device displays an image from the first 3D CT representation.

In some embodiments, a depth sensor captures the surface data. In other embodiments, a camera captures where the surface data is based on optical measurements.

Various parameters or combinations of parameters may be used to assist in estimation of the 3D CT representation. In one embodiment, the segmentation of an organ or anatomy is used. The 3D CT representation is generated in response to the input of the surface data and the segmentation. In another embodiment, both the segmentation and landmark location are determined. The 3D CT representation is generated in response to the input of the surface data, the segmentation, and the landmark location. The parameter information may be derived from the surface data or from scan data from a different medical imaging modality than CT.

In one embodiment, stacked networks are used. A second machine-learned generative network outputs a segmentation map and/or landmark location map in response to input of the surface data and a second 3D CT representation of the patient. The first machine-learned generative network generates the first 3D CT representation in response to input of the segmentation map as the segmentation and/or the landmark location map as the landmark location and input of the surface data. The second 3D CT representation is formed from an output of a third machine-learned generative network or from an output of the first machine-learned generative network. The first and second machine-learned generative networks may be iterative used.

The 3D CT representation may be generated for only anatomy of interest despite other anatomy being in the represented volume. The first 3D CT representation is generated as a representation of first internal anatomy without second internal anatomy. Multi-channel output may be used, such as generating a second 3D CT representation of the second internal anatomy without the first internal anatomy.

The first 3D CT representation is generated as a voxel or mesh representation.

In a further embodiment, a medical scanner is configured based on the first 3D CT representation. The medical scanner images the patient as configured based on the first 3D CT representation.

In a second aspect, a method is provided for computed tomography (CT) prediction from surface data in a medical imaging system. A sensor captures an outer surface of a patient. An image processor generates a first three-dimensional (3D) CT representation by first and second machine-learned networks in response to input of the surface data to the first and second machine-learned networks. The surface data is from an output of the sensor for the outer surface. The first machine-learned network outputs a spatial segmentation, and the second machine-learned network outputs the first 3D CT representation based on the surface data and the spatial segmentation. A display device displays an image from the first 3D CT representation.

In one embodiment, the first machine-learned network is configured to output the spatial segmentation and a landmark map, and the second machine-learned network is configured to output based on the surface data, the spatial segmentation, and the landmark map. In another embodiment, the first 3D CT representation is generated from one of one or more output channels, where each output channel representing different ones of only muscle, only skeleton, only vessel, only organ, and only a tissue type.

In a third aspect, a medical imaging system is provided for computed tomography (CT) prediction. A depth sensor is configured to measure depths to a patient. An image processor is configured to apply a machine-learned model to depth information from the depths. The machine-learned model was trained to generate a CT volume of a first type of anatomy and not a second type of anatomy despite the second type of anatomy being within the CT volume. A display is configured to display an image from the CT volume.

In a further embodiment, a magnetic resonance or ultrasound scanner is configured to scan the patient. The machine-learned model generates the CT volume in response to input of the depth information and a segmentation and/or landmark location from the scan of the patient.

In another embodiment, the machine-learned model includes multiple output channels including a first channel for the first type of anatomy and a second channel for the second type of anatomy.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EMBODIMENTS

Figure 1:
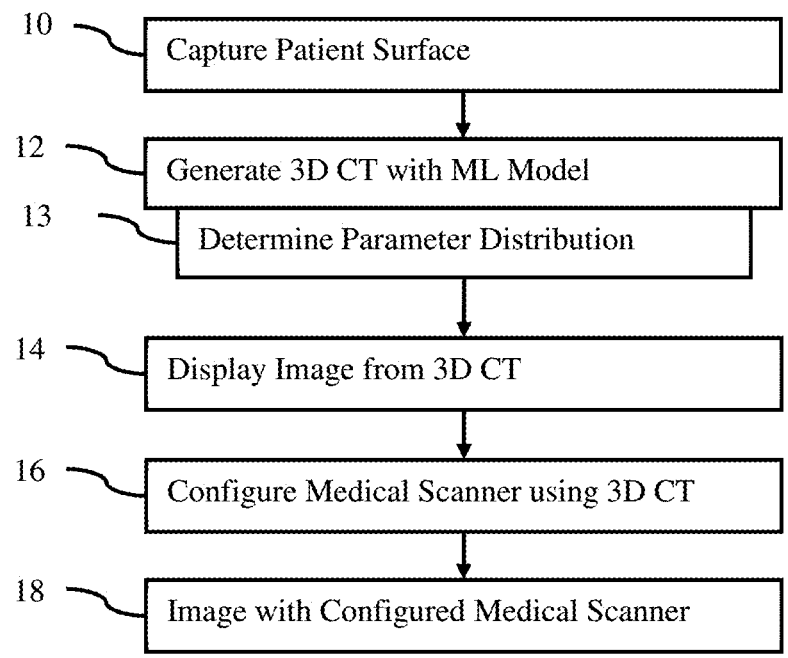
FIG. 1 is a flow chart diagram of one embodiment of a method for 3D CT representation prediction from surface data in a medical imaging system.

The internal anatomy of a human body is estimated from the surface data. A 3D CT representation is predicted from patient surface data. For example, synthetic CT representation of a volume of a person is generated from the surface geometry or depth camera measurements. The 3D CT representation of the internal anatomy of a patient is predicted from geometric measurements on the patient's body surface using deep machine learning algorithms. The synthetic CT serves as an approximation of the true internal anatomy.

Using only surface data may lead to errors. Parameterization is used to reduce errors. Synthetic parameterized CT is generated from the surface geometry. The synthetic CT is predicted together with a set of parameters, which can be further updated to correct the original prediction. The generated CT representation may have one or more types of parameters for updating, including body markers (landmarks) and/or segmentation. The parametrization is learned using deep learning. Multiple kinds of parametrization, such as markers and/or segmentation, may be used. Multiple types of parameters may be used at the same time. The locations or maps for one or more of the parameters may be learned from and/or used in application information from external acquisitions, such as locating landmarks or segmentation from a previous magnetic resonance or ultrasound scan.

The parametrized 3D representation of the human internal anatomy predicted from the surface geometry allows various options. Different representation of the internal anatomy (e.g., muscles-based, skeleton-based, vessels-based . . . ) may be output, creating a CT volume with one type of anatomy and not another. A multi-channel output may be used to separately predict 3D CT representations of different types of anatomy at a same time with consistent spatial distribution. The 3D CT representation may be a voxel-based or mesh-based representation. Since machine-learned models are used, the generation of the 3D CT representation may be performed quickly and is scalable.

With the proposed framework, synthetic CT volumes may easily be generated by varying surface geometry. By perturbing the parameters, additional synthetic 3D CT representations may be generated from the same surface geometry. As a result, the training data barrier in the medical domain is overcome by producing many 3D CT representations through parameter adjustment. Since the spatial parameters perturb the 3D CT representation, the predicted representation of the internal anatomy is a parametrized image. The predicted 3D CT representation may be manipulated using parameters distributed across the body. For example, if the predicted lung appears short, then a body marker or segmentation near the lung region may be manipulated to adjust its position, size, or shape, and the 3D CT representation will be updated in a physically consistent manner.

In one embodiment, parametrized images are generated using a convergent training pipeline. As the training framework learns to predict CT volumes and the corresponding spatial parameters (e. markers or segmentation), the framework also needs to ensure that the perturbations of these parameters lie on a manifold of 'realistic deformations' (e.g. realistic body anatomy when generating synthetic CT). Since learning such output spaces, which are implicitly highly correlated, is difficult, a pair of networks is trained, one trained to predict the parameters from CT volume contents and the other trained to predict the CT volume contents from the parameters. When the parameters are updated, the networks are applied iteratively in a loop until convergence. To facilitate such convergent behavior during test phase, both networks are jointly learnt. A bijection between the predicted markers and the generated images is explicitly learned.

The predicted 3D CT representation may be useful for teaching purposes, such as generating 3D CT representation as samples to be used in machine training to avoid a data barrier of too few samples for training. The predicted 3D CT representation may be used for scan planning. For example, the generated 3D CT representation is used for more precise positioning compared to just using body markers. Furthermore, positioning suggested by the system using a physically consistent generated 3D CT representation may be more readily used by radiographers as opposed to just the body marker points on the exterior of the patient. The 3D CT representation may be used for detection of anomalies, patient positioning, interventional procedures, completion of a full CT from a partial CT, or other uses.

FIG. 1 is a flow chart diagram of one embodiment of a method for computed tomography (CT) prediction from surface data in a medical imaging system. A machine-learned model is used to generate 3D CT from data representing an outside of the patient. Parameterization, such as by segmentation and/or landmark location, is used to assist in generating the 3D CT. The 3D CT represents internal organs of the patient volumetrically.

The method is performed in the order shown (e.g., top to bottom or numerical), but other orders may be used. Additional, different or fewer acts may be provided. For example, acts 16 and/or 18 are not provided. In another example, act 14 is not provided as the 3D CT representation is one of many used for machine training or is used to configure for imaging without viewing by the operator.

Figure 6:
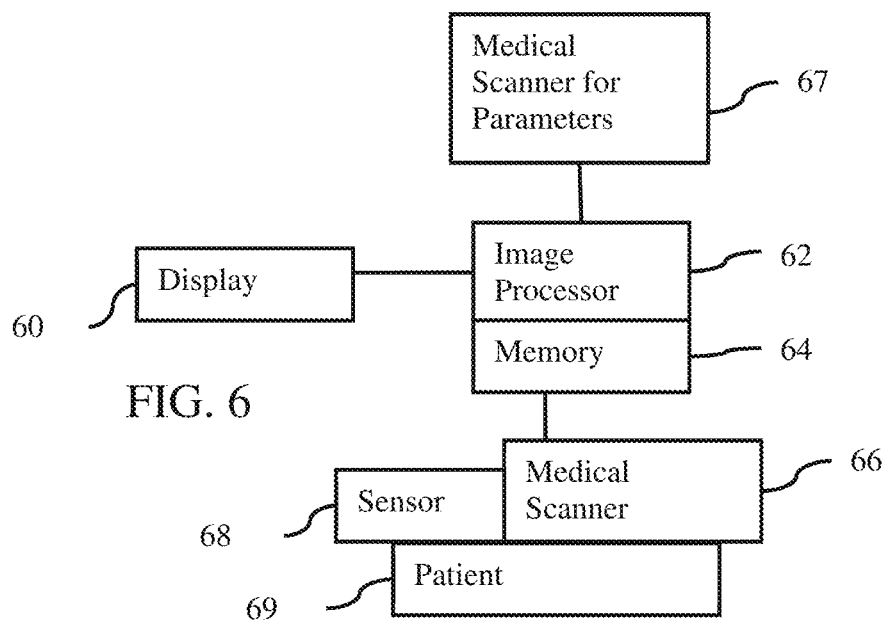
FIG. 6 is a block diagram of one embodiment of a system for 3D CT representation prediction.

The method is implemented by the medical imaging system of FIG. 6 or a different medical system. For example, a depth camera performs act 10. A computer, such as for a medical imaging system, performs acts 12 and/or 16. A display performs act 14. A medical scanner performs act 18 and is controlled in act 16.

In act 10, a sensor captures an outer surface of a patient. The sensor is a depth sensor, such as a 2.5D or RGBD sensor (e.g., Microsoft Kinect 2 or ASUS Xtion Pro). The depth sensor may be a camera or cameras capturing a grid projected onto the patient. Multiple cameras may reconstruct an outer surface from multiple images without transmission of structured light. Other optical or non-ionizing sensors may be used.

The sensor is directed at a patient. The sensor captures the outer surface of the patient from one or more perspectives. Any portion of the outer surface may be captured, such as the entire patient from head to toe and hand to hand on one side or just the torso.

The outer surface is the skin of the patient. In other embodiments, the outer surface includes clothing. The sensor may use a frequency that passes through clothing and detects skin surface.

The outer surface is captured as depths from the sensor to different locations on the patient, an image or photograph of the outside of the patient, or both. The sensor outputs the sensed image and/or depths. Alternatively, the sensor measurements are processed to determine the outer surface information, such as stereoscopically determining the outer surface from camera images from different angles with image processing.

The measurements of the outer surface from the sensor are surface data for the patient. In one embodiment, the measurements or other output of the sensor are used to determine the surface data. The output is processed to determine the surface data. For example, a statistical shape model is fit to the depths. The statistical shape model is a mesh or other representation of an average or other statistical representation of an outside of a human or part of a human. The statistical shape model includes probabilities or other constraints on alteration, so that the fitting maintains the shape based on statistics. The surface data is then determined from the fit statistical shape model, such as depths from a point to the model.

The surface data may include different representations of the patient, such as the depths from the fit model and a projection of the outer surface (e.g., a camera image) or a thickness. The thickness may be a difference of a given depth from the maximum and minimum depth for the model or the depths from the sensor. For example, given a 3D surface mesh of a patient, 2D projections of the data are generated as a skin surface image and a depth image. As another example, the 3D human surface mesh data is represented with a 2-channel 2D image—the first channel stores the depth of the body surface as observed from front, and second channel stores the thickness computed by measuring the distance between the closest and furthest point as observed from front. Other surface data may be used.

The 3D CT representation is predicted from the surface data. The 3D CT representation shows the internal patient anatomy. The 3D CT representation may be predicted from only the surface data or may be predicted from the surface data and other data, such as patient height, weight, or body mass index.

Figure 2:
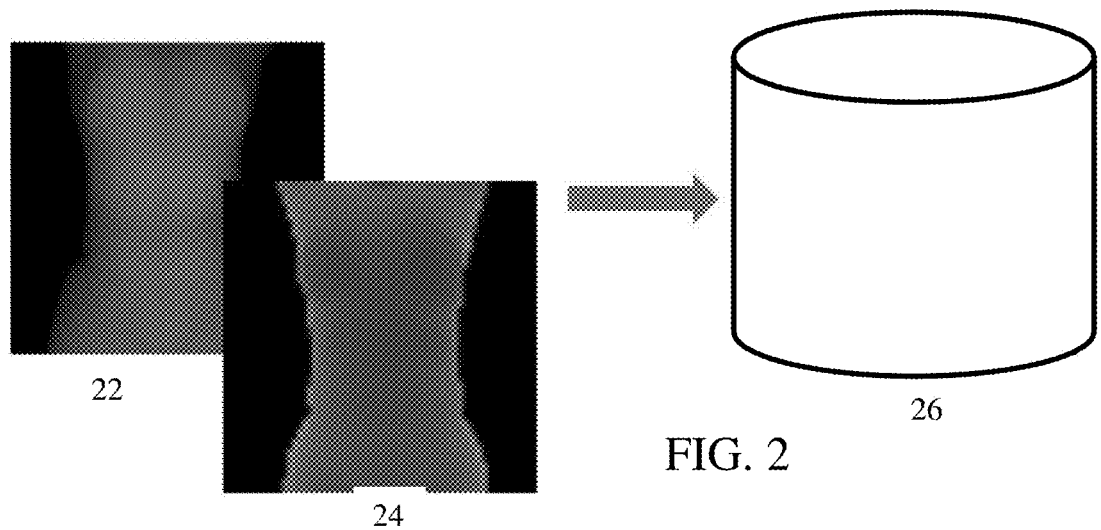
FIG. 2 illustrates example 2-channel surface data for predication of a 3D CT representation.

In act 12, an image processor generates the 3D CT representation. The surface data with or without other data are input to a machine-learned network and scalar values for the 3D CT representation are output. For example, a projection image and depth image of the outer surface are input as two channels to the machine-learned network, which outputs a synthetic 3D CT representation in response to the input. FIG. 2 shows an example where a surface depth image 24 and a surface projection image 22 are input to output a 3D CT representation 26. The image processor applies the machine-learned network for 3D CT representation prediction. Any inputs for which the network is trained to use are applied as an input feature vector.

The machine-learned network is a generative network for generating a spatial distribution from an input spatial distribution. For example, the generator is an image-to-image network, such as a generative adversarial network, trained to convert surface data to a 3D CT representation. The trained convolution units, weights, links, and/or other characteristics of the network are applied to the surface data and/or derived feature values to extract the corresponding features through a plurality of layers and output the 3D CT representation. The features of the input images (e.g., surface data) are extracted from the images. Other more abstract features may be extracted from those extracted features using the architecture. Depending on the number and/or arrangement of units or layers, other features are extracted from the input.

For training the machine-learned network, the machine learning network arrangement is defined. The definition is by configuration or programming of the learning. The number of layers or units, type of learning, and other characteristics of the network are controlled by the programmer or user. In other embodiments, one or more aspects (e.g., number of nodes, number of layers or units, or type of learning) are defined and selected by the machine during the learning.

Figure 3:
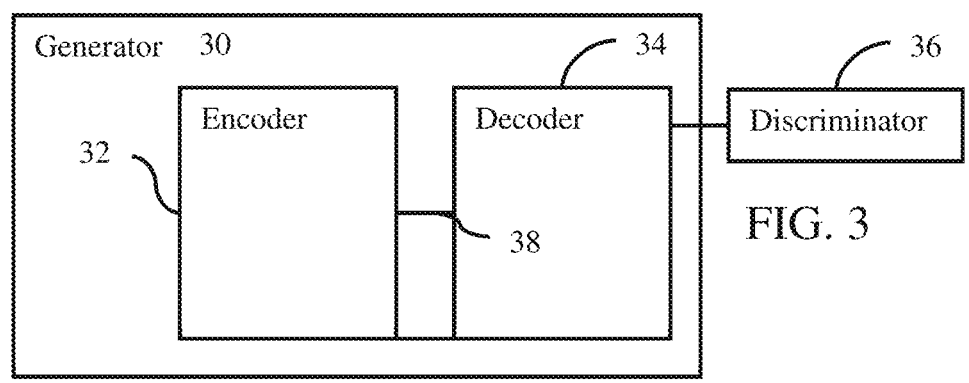
FIG. 3 is a block diagram of one embodiment of a GAN.

Any machine training architecture for outputting a 3D spatial distribution from an input 3D spatial distribution may be used. For example, U-Net is used. A convolutional-to-transposed-convolutional network is used. FIG. 3 shows an example fully convolutional network as a GAN. The GAN includes a generator 30, such as the image-to-image or U-Net, and a discriminator 36. The generator 30 includes an encoder (convolutional) network 32 and decoder (transposed-convolutional) network 34 forming a "U" shape with a connection between passing features at a greatest level of compression or abstractness from the encoder 32 to the decoder 34. One or more skip connections 38 may be used to pass values of features between the encoder 32 and decoder 36 other than at the bottleneck. Any now known or later developed U-Net architectures may be used. Other fully convolutional networks may be used.

For application, the generator 30 of the GAN is used without the discriminator 36. The GAN is applied to the patient surface data by the generator 30 without the discriminator 36. The discriminator 36 is used for training. In alternative embodiments, the generator 30 is trained without a discriminator (e.g., non-GAN image-to-image network or U-Net).

The GAN is a deep architecture, which may include convolutional neural network (CNN) or deep belief nets (DBN). Other deep networks may be used. The network is defined as a plurality of sequential feature units or layers.

Sequential is used to indicate the general flow of output feature values from one layer to input to a next layer. The information from the next layer is fed to a next layer, and so on until the final output. The layers may only feed forward or may be bi-directional, including some feedback to a previous layer. The nodes of each layer or unit may connect with all or only a sub-set of nodes of a previous or subsequent layer or unit.

Rather than pre-programming the features and trying to relate the features to attributes, the deep architecture is defined to learn the features at different levels of abstraction based on an input image with or without pre-processing. The features are learned to reconstruct lower level features (i.e., features at a more abstract or compressed level).

In one embodiment, the 3D CT representation prediction is treated as an image-to-image translation problem. Starting from 2 channel images (e.g., skin surface and depth to skin image), a single channel image of the same size (3D CT representation) is regressed. This approach provides a network able to capture the features in the input to retrieve the output, which consists, in a sense, of a more 'complete' version of the input. A Fully Convolutional Networks (FCN) may be used, such as the generator 30 with the encoder 32 and the decoder 34. The encoder 32 'encodes' the useful features of the input needed to regress the target, while the decoder 34 tries to use these features to create the targeted image.

Figure 4:
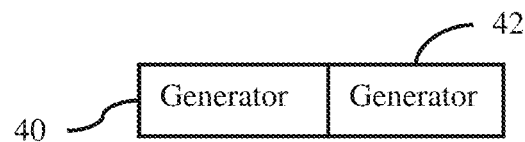
FIG. 4 shows an example stacking of two generators.

In another embodiment, multiple generators are stacked, such as stacking multiple image-to-image networks, encoder-decoders, U-Nets or GANs. For example, the generators 40, 42 are stacked sequentially as shown in FIG. 4. The output from an initial generator 40 provides an input to the later generator 42, which outputs the 3D CT representation. The initial generator 40 receives the surface data and/or a previous 3D CT representation as an input.

Stacking generators 30 helps capture more details for the 3D CT representation. The patient's shape may be regressed with more details, such as details around or of the lungs. The initial generator 40 parameterizes some aspect reflected in the 3D CT representation, such as a segmentation, landmarks, anatomy, internal arrangement, or other characterization providing a spatial relationship other than the outside surface or skin. This other information may be used in 3D CT representation prediction. Rather than focus on 3D CT representation regression in both generators 40, 42, the stacked network uses at least one generator 40 to predict one or more internal body markers, segmentation, or other spatial relationship. External body markers may be detected or predicted. The input surface data as well as the predicted internal parameterization are used to predict 3D CT representation by another generator 42. The predicted parameters may be adjusted, which would automatically update the 3D CT representation.

Figure 5:
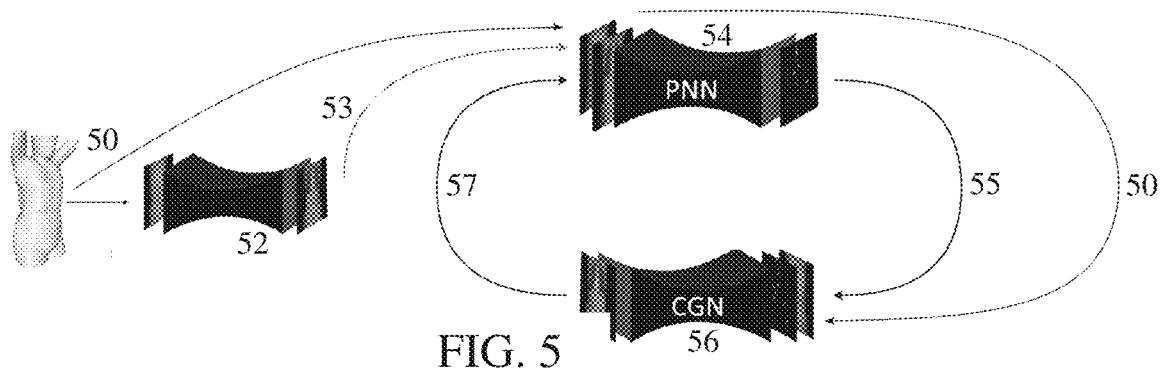
FIG. 5 shows an example embodiment of stacked networks with parameterization included as part of 3D CT prediction.

FIG. 5 shows an example of stacked machine-learned networks (e.g., generative networks) using parameterization. FIG. 5 shows a training pipeline and/or generators for application in a parametrization framework.

Three generators 52, 54, 56, such as U-Nets or encoder-decoders, are shown, but additional, different, or fewer generators may be used. For example, the generator 52 is not provided. The surface data 50 is used as input to all three generators 52, 54, 57. The initial network or generator 52 generates an initialization of the 3D CT representation, such as a full CT scan. The generator 54 is a parameterization network trained to parameterize, such as generate a segmentation (e.g., voxel labels or mesh of a surface for an organ, tissue, anatomy, or internal system in 3D), landmarks (e.g., one or more anatomical reference points positioned in 3D), or another parameterization. The generator 54 receives a 3D CT representation 53 or 57 and the surface data 50. In response to input, the generator 54 outputs a representation of the location or locations of internal anatomy, such as segmentation, landmarks, or another parameterization. The internal anatomy is represented in a 3D space, giving information about the patient internal structures. The generator 56 receives the parameterization 55 and surface data 50. In response, the generator 56 outputs a current 3D CT representation 57. The generator 56 is a conditional generation network for predicting the 3D CT representation (e.g., voxel or mesh representing X-ray attenuation, measures of Hounsfield units, or tissue density in a volume of the patient).

The generation of the 3D CT representation may be iterative. The initial 3D CT representation 53 used by the parameterization generator 54 is from the generator 52. Subsequent iterations use the output 3D CT representation 57 of the generator 56 as input to the parameterization generator 54. After a given number of iterations or reaching another stop criteria (e.g., measure of convergence), the final 3D CT representation 57 output by the generator 56 is used. In other embodiments, a template or default 3D CT representation, noise, or a 3D CT representation generated by the generator 56 with a template or default parameterization 55 is used as the initial 3D CT representation instead of output from the generator 52.

In application, an image processor generates a 3D CT representation using two or more machine-learned networks (e.g., generators 52, 54, 56). The 3D CT representation is generated in response to input of the surface data to the machine-learned network or networks. One or more of the machine-learned networks may operate without input of surface data.

Using the stacked machine-learned networks, the 3D CT representation is generated in act 12 based, in part, on the parameterization of act 13. The image processor determines an internal spatial distribution based on the surface data. For example, a segmentation and/or a landmark location is determined. Segmentation for one or more anatomical objects and/or one or more landmarks for a corresponding one or more points or regions may be determined.

The generator 54 outputs the parameterization as a map, such as a probability or heatmap. In response to input of the surface data 50 and a 3D CT representation 53, 57, a segmentation map and/or landmark location map are estimated for the patient. The generator 54 is trained to predict the parameterization based on surface data and estimate of the 3D CT representation.

In one embodiment, the parameter prediction network (i.e., generator 54) takes the surface image 50 as well as the predicted CT volume 53, 57 as input and predicts the locations for all the parameters. The network is a U-Net like architecture trained to regress from a 3-channel input image (2 surface data channels, 1 CT volume channel) to an N-channel heatmap volume by minimizing L2-loss or other loss. N corresponds to the number of landmarks, segmentations, and/or parameterizations, such as a heatmap corresponding to 17 anatomically meaningful landmarks. The heatmap is a spatial distribution of likelihood of any given voxel being the landmark. For the heatmaps, each output channel compares with the given ground truth that includes a Gaussian mask (e.g., kernel radius=5, $\sigma=1$) centered at the given target location. Other radii and standard deviations may be used. Other images or spatial distributions than a heatmap may be used, such as providing binary labels for each landmark, segmentation, or other parameterization.

In one embodiment, the generator 54 is not used. Instead, the parameterization (e.g., segmentation and/or landmark location(s)) are provided from scanning. A non-CT imaging modality may be used. For example, magnetic resonance or ultrasound scanning is performed. Image processing is applied to identify the spatial information (e.g., segmentation or landmarks) for the patient from the non-CT scan. CT imaging may be used. For example, a previous CT scan of a patient is used to locate the segments and/or landmarks. All or only some of the segmentation and/or landmarks may be identified from these other sources (e.g., previous patient scans). The parameters are extracted, at least in part, from complete or partial scans of the patient rather than estimated from the surface data. The surface data may be used to estimate the locations of any missing parameterization.

In act 12, the image processor generates the 3D CT representation of the patient by a machine-learned generative network (e.g., generator 56) in response to input of the surface data 50 and the segmentation and/or landmark location 55 to the machine-learned generative network. The parameters 55 are input to the Conditional Generation Network (CGN), which generates the 3D CT representation. The new 3D CT representation 57 can then go back to the parameters neural network (PNN or generator 54) in the iterative pipeline.

In one embodiment, the conditional generation network is a conditional GAN architecture. In one embodiment, a Wassertein GAN architecture conditioned on the skin surface is used. The generator with the U-Net architecture takes the surface image and parameter heatmap(s) as input and outputs the synthetic 3D CT representation. To stabilize the training, a Wasserstein loss with gradient penalty is used. Other losses with or without a gradient penalty may be used. The critic or discriminator takes the surface image and corresponding 3D CT representation as input. Alternatively, the critic or discriminator receives the surface images, parameter maps (parameter space) and 3D CT representation as input to implicitly force a strong correlation between them.

The generator 56 is trained to receive the segmentation, landmark location(s), and/or other parameterization 55 as input. Any combination of heatmaps representing spatial distribution of internal structure or anatomy may be used. Surface data 50 is also input to estimate the 3D CT representation for the patient. The estimate may be provided without any or without additional scanning of the patient.

The 3D CT representation is output as a voxel or mesh representation. For voxels, estimates of the CT attenuation or tissue density are output for the voxels distributed over three dimensions. A voxel-based representation allows a floating-point representation in a 3D space. For a mesh, one or more 3D surfaces of internal objects and/or the skin are estimated. A triangular or other mesh (e.g., nodes connected by edges) is output. Each 3D volume, whether representing the surface data or an organ, may be represented in different ways. A mesh representation allows an efficient compact representation of any volume, together with a high-dimensional set of parameters, giving best control on the shape representation.

More than one output channel or corresponding 3D CT representation may be generated. Since the 3D CT representation is synthetic, the generator 56 may be trained to generate different aspects or sub-parts of the patient volume. For example, the 3D CT representation may estimate for one type of anatomy and not another. As another example, different 3D CT representations may be generated where each represents different anatomy or types of tissue. Since the same generator 56 is used to output on different channels, the generated 3D CT representations are more likely consistent between or relative to each other. The different anatomy may be different ones of only muscle, only skeleton, only vessel, only organ, and only a tissue type. A given 3D CT representation may represent one or more different tissues, anatomy, objects, or systems and not one or more other tissues, anatomy, objects, or systems. In one embodiment, a per-organ multi-channel 3D volumes are output. Each channel represents a mask or CT values of the corresponding organ. The overall CT may be reconstructed using the Hounsfield Unit (e.g., X-ray attenuation or tissue density) values of each organ. In another embodiment, a per-anatomical system multi-channel 3D volumes are output. Each channel represents an anatomical system, such as muscles, skeleton, breathing, vessels, cardiac, digestive, and/or another system. Alternatively, the 3D CT representation is a full representation (i.e., 1 channel outputting an estimate of CT for the patient).

For training, many samples of training data (e.g., surface data, ground truth parameterization (e.g., segmentation or landmarks), and ground truth 3D CT representation) are used to learn to output the 3D CT representation from input surface data. The machine learning models are trained to learn the correspondence between the surface data and the 3D CT representation.

One or more of the generators 40, 42, 52, 54, 56 may be pre-trained. For example, the network for parameterization (i.e., generator 54) may be a pre-trained spatial relationship regressor. As the generator 56 for predicting the 3D CT representation is trained, the weights of the network for parameterization are not updated. During training, the ground truth parameterization (e.g., segmentation and/or landmark location) may be used for training the generator 56 for the 3D CT representation rather than parameterization output by the network or generator 54. Alternatively, both networks 54, 56 are trained end-to-end or during a same training and/or the landmark output of the network 54 is used in training the network 56. For GAN, each generator 40, 42 may be trained with a separate discriminator or one discriminator is used for the combination of generators (i.e., combination of GANs).

Any batch size may be used in training. In one embodiment, the batch size is 32 examples. In another embodiment, the batch size is 1 example. Smaller batch size may lead to higher loss and mean square error.

For training any of the networks, various optimizers may be used, such as Adadelta, SGD, RMSprop, or Adam. The weights of the network are randomly initialized, but another initialization may be used. End-to-end training is performed, but one or more features may be set. Batch normalization is used. Dropout, and data augmentation are not used, but may be (e.g., using batch normalization and dropout). During the optimization, the different distinguishing features are learned.

The optimizer minimizes an error or loss, such as the Mean Squared Error (MSE), Huber loss, L1 loss, or L2 loss. The Huber loss may be less sensitive to outliers in data (represented in the training set by big variations in shape). Use of Huber loss helps capture better context. The patient's shape may be regressed better. In another embodiment, an L1 loss is used to better define lungs or other organs represented in the generated 3D CT representation. Using stacked U-Nets with L1 loss, the patient's shape and details for the lungs or other organs may be better than for Huber or L2 loss.

The stacked pipeline of FIG. 5 is trained sequentially, simultaneously, and/or end-to-end. In one embodiment, loss from CGN (i.e., generator 56) is back propagated to PNN (i.e., generator 54), and loss from PNN is back propagated to CGN. As a result, both models converge to a consistent state. Other training approaches may be used. In one embodiment, the parameterization and 3D CT representation networks 54, 56 are separately pre-trained using the available ground truth data. The network 54, 56 are subsequently refined end-to-end to minimize the combined loss, defined as, $L=L_{PNN}+L_{CGN}$ where, $L_{PNN}$ is the mean squared error (MSE) between the predicted and the ground truth heat maps for the parameterization and $L_{CGN}$ is a combination of the L1 loss and optionally any additional adversarial loss between the predicted and ground truth CT volume.

For pre-training the parameterization network 54 (e.g., segmentation or landmark prediction), the Adam or other optimizer minimizes the MSE loss. The initial learning rate is $10^{-3}$. During pre-training, the ground truth 3D CT representation with body surface images (i.e., surface data) are used as inputs. During the convergent training process, the input is replaced by the predicted 3D CT representation. This initially worsens the performance on the parameter prediction network, but the network recovers after a few epochs of convergent training.

For pre-training the 3D CT representation network 56 (i.e., CGN GAN), surface images and ground truth parameter maps are input, using the Adam or other optimizer with an initial learning rate of $10^{-3}$. After pre-training, the RMSProp or other optimizer with a low learning rate of $10^{-5}$ is used. The gradient penalty variant of Wasserstein GAN (WGAN) may outperform the original WGAN with weight clipping. The architecture of the critic is similar to the encoder section of the generator network. In the case of WGAN, using a more complex critic may help training converge more quickly. During the convergent training, the network is iteratively updated using the predicted landmarks as input.

For the convergent training via iterative feedback, both networks are iteratively applied in succession until both reach the steady state during the test phase. This implicitly requires the networks to have a high likelihood of convergence during the training stage. A stable solution sits where both the parameters and synthetic CT volume are in complete agreement with each other, suggesting a bijection. One network is frozen while updating the weights of the other network using its own loss as well as the loss backpropagated from the other network. Thus, not only the networks get feedback from the ground truth, the networks also get feedback on how they helped each other (e.g., good parameters give good 3D CT representation, and vice versa). The losses optimized by conditional image generation (CGN) and parameter neural network (PNN) at each iteration are given by: $L_{CGN}=L_{adv}(V_{gt}, V^i_{syn})+L_2(PPN(V^i_{syn}, S), P_{gt})$ and $L_{PNN}=L_2(P^i, P_{gt})+L_1(V_{gt}, CGN(P^i, S))$ where, CGN(.) and PNN(.) are deep networks depicted in functional form, $V_{gt}$ and $P_{gt}$ are ground truth CT volume and parameter heat maps respectively, and $V^i_{syn}$ and $P^i$ are predicted volumes and parameter heat maps at iteration i. The iterative approach to train the networks to facilitate convergence is through learning to cooperate instead of competing. Similar to GAN training, there is a possibility that the training may become unstable and diverge. The losses are weighted with a scale to avoid divergence. While the number of epochs required to reach convergence depends on how tightly the output of the two networks correlate, 50 epochs may be sufficient. Other numbers of epochs may be used. No significant (e.g., threshold amount) change in CT or in landmarks positions suggests or indicates convergence.

To validate the convergent training, a random data sample is selected from the testing set, and the parameter displacement across iterations is monitored. Without the convergent training, the parameters may change across iterations.

With the stacked pipeline in FIG. 5, one or more of the parameter locations may be moved by the user or by image processing. User input or processor input is received, such as by manual entry to adjust a landmark location or segmentation using a user interface. As a result, the parameter map for that channel is altered. Upon input to the 3D CT representation generator 56, the 3D CT representation generator 56 outputs a 3D CT representation based on the altered parameter map. To update the 3D CT representation, the other parameters may move in a constrained fashion. For example, the lung bottom cannot be below the kidneys since that's physically not a possible setup. By reusing the predicted 3D CT representation from the generator 56 in the stacked pipeline, the networks 54 and 56 ensure that the parameters and 3D CT representation are consistent. If a parameter location is updated, the rest of the parameters are appropriately updated (if needed) by cycling the resulting 3D CT representation through the parameter network 54 and again predicting a 3D CT representation by the 3D CT representation network 56 based on the output parameter maps. The 3D CT representation ensures physical correctness.

The stacked pipeline of FIG. 5 provides a volume (e.g., 3D CT representation) parametrized by a set of spatially distributed markers or segmentations. One or more of the parameters may be manipulated in size, shape, and/or location while still providing realistic 3D CT representations. The manipulation of spatial parameters uses learning a bijection mapping. The parameter neural network (PNN) (i.e., network 54) is trained to predict the parameters from the volume content, and the Conditional Generation network (CGN) (i.e., network 56) is trained to predict the CT volume contents given the parametrization. After initial predictions, the networks 54, 56 are iteratively applied (i.e., current output used as input in repeating cycles) until convergence. While parametrized volumes may be generated from noise, conditional generation as naturally applied to the task of generating the CT volumes from 3D body surface data is used.

Referring again to FIG. 1, a display device displays the 3D CT representation in act 14. Where several iterations of the 3D CT representation are generated, the 3D CT representation after a given number of iterations and/or convergence is displayed. Other predicted 3D CT representations may be displayed.

The display is a visual output. The image processor generates an image. A 3D CT representation is used to generate an image, which is displayed on the display. The image may be output to a display, into a patient medical record, and/or to a report.

The 3D CT representation is used to form an image. The image is generated from the scalar values or intensities of the 3D CT representation. The scalar values are mapped to display values, such as RGB values. A grayscale or color image of the 3D CT representation is generated. In other embodiments, the 3D CT representation is predicted as display values. Since the 3D CT representation is a volume, the image is a 2D image of a planar region in the volume and/or a three-dimensional rendering from the volume. Any 3D CT imaging may be used. The image of the 3D CT representation shows the patient shape as well as positions of one or more organs. One or more parameters (e.g., landmarks or segmentation) may be highlighted.

The 3D CT representation may be used for diagnosis or other purpose by the user. For example, the 3D CT representation is used to position a patient, such as moving the patient along a longitudinal axis so that a given landmark or organ is centered with respect to the medical scanner.

In act 16, the image processor configures the medical scanner based on the 3D CT representation. The medical scanner may configure itself. The landmarks, segmentation, or other parameterization may be used, or organ location is detected from the 3D CT representation. Alternatively, the user configures the medical scanner based on the 3D CT representation by entry with one or more controls.

The prediction of certain internal anatomical structures may assist in planning a medical scan. The 3D CT representation may be used to plan for scanning by any modality, such as CT, MR, fluoroscopy or ultrasound. For CT scanning, the 3D CT representation may be used to determine the scan range to obtain 3D CT representation or full CT scan, depending upon which organ needs to be scanned and how accurately the nearby structures may be predicted. The location of internal anatomical structures reflected in the 3D CT representation may assist is coil placement for MR scanning. For ultrasound scanning, the 3D CT representation may assist in the probe guidance by providing approximate position of the various organs. For fluoroscopy using dyna-CT scans, the 3D CT representation may be useful for positioning the patient and/or the scanner.

As radiation exposure is considered harmful, X-ray images are often acquired with a limited field of view, only covering a certain body region (e.g., thorax or abdomen). Using parametric images, the 3D CT of the entire body may be reconstructed or predicted such that the predicted 3D CT representation is consistent with the partial yet real CT data from a CT scan. The reconstructed 3D CT representation may be used for acquisition planning in subsequent or future medical scans. Using the reconstructed 3D CT representation, the scan region may be specified more precisely, thus potentially reducing the radiation exposure.

To reconstruct the complete 3D CT, a parametrized volume of the patient is generated from the surface data. The predicted 3D CT representation may not always correspond to the true internal anatomy. Using the parameter locations, the parameter locations may be adjusting until the synthetic 3D CT representation matches the real one where they overlap. Once the parameters are adjusted, the complete 3D CT representation is generated together with all the parameters.

The predicted 3D CT representation may be used for anatomical anomaly detection. The predicted 3D CT representation generates a representation of healthy anatomy learned from healthy patients. A real or actual CT of the patient may be compared with the predicted 3D CT representation. By quantifying the difference between the real and the predicted, any anatomical anomalies may be detected. For example, a missing lung or an added implant are highlighted by subtraction. While the anatomical anomaly is easier to identify, the proposed approach with higher resolution imaging may be used to suggest candidates for lung nodules or other pathological conditions.

Due to privacy and health safety issues, medical imaging data is difficult to obtain, which creates a significant barrier for data driven analytics such as deep learning. The 3D CT representation prediction may be employed to generate realistic training data. The ability to spatially reposition the parameters and generate a corresponding 3D CT representation is used to create a varied sampling for training. Parametrized 3D CT representations offer an approach to generate medical image training data. The spatial parametrization offers controlled perturbations such as generating data variations with lungs of certain sizes. For tasks such as marker detection, since the image manifold is smooth, it's possible to generate training data (for augmentation) together with annotations, by annotating the marker in one image and tracking it in the image domain as it is perturbed along the image manifold.

In act 18, the configured medical scanner scans the patient. The patient is imaged. The imaging is performed based on the configuration of the medical scanner. The scan range, focus, field of view, intensity, scan pattern, filtering, image processing, and/or other imaging parameters are based on the 3D CT representation, so the scanning is based on the 3D CT representation. The resulting image from the scanning more likely shows the region of interest. Ionizing radiation from the scanning may be limited based on the configuration using the 3D CT representation.

FIG. 6 shows a medical imaging system for 3D CT representation prediction. The medical imaging system implements the method of FIG. 1. The system uses the stacked machine-learned models of FIG. 4 or 5. Other stacked models providing estimation of parameterization and 3D CT representation from surface data may be used.

The medical imaging system includes the display 60, memory 64, and image processor 62. The display 60, image processor 62, and memory 64 may be part of the medical scanner 66, a computer, server, workstation, or other system for image processing medical imaging information. A workstation or computer without the medical scanner 66 may be used as the medical imaging system. The medical imaging system also includes the sensor 68 for sensing an outer surface of a patient.

Additional, different, or fewer components may be provided. For example, a computer network is included for remote 3D CT representation generation of locally captured surface data or for local 3D CT representation generation from remotely captured surface data. The network is applied as a standalone application on the workstation or a local device or as a service deployed on network (cloud) architecture. As another example, a user input device (e.g., keyboard, buttons, sliders, dials, trackball, mouse, or other device) is provided for user alteration or placement of one or more markers (e.g., landmarks).

The sensor 68 is a depth sensor. LIDAR, 2.5D, RGBD, stereoscopic optical sensor, or other depth sensor may be used. One sensor 68 is shown, but multiple sensors may be used. A light projector may be provided. The sensor 68 may include a separate processor for depth measurements from images, or the image processor 62 determines the depth measurements from images captured by the sensor 68.

The sensor 68 is directed to the patient 69. The sensor 68 may be part of or connected to the medical scanner 66 or is separate from the medical scanner 66.

The sensor 68 is configured to measure depths to a patient. The depths are distances from the sensor 68 or other location to the patient at various locations on the patient. Any sample pattern over the patient may be used. The sensor 68 outputs depth measurements and/or a surface image. The image processor 62 or another processor may fit a model to the sensor output to provide surface data. Alternatively, the sensor 68 outputs the surface data as the measurements.

In one embodiment, the parameterization (e.g., segmentation or landmark) estimation is performed by application of a machine-learned model. In another embodiment, the medical scanner 67 provides parameterization. For example, a magnetic resonance, ultrasound, CT, or another medical scanner scans a patient. The scan data is image processed to identify spatial relationships, such as a segmentation of an organ and/or locations of landmarks.

The image processor 62 is a control processor, general processor, digital signal processor, 3D data processor, graphics processing unit, application specific integrated circuit, field programmable gate array, artificial intelligence processor, digital circuit, analog circuit, combinations thereof, or other now known or later developed device for applying a machine-learned model to depth information. The image processor 62 is a single device, a plurality of devices, or a network. For more than one device, parallel or sequential division of processing may be used. Different devices making up the image processor 62 may perform different functions, such as applying different generators by one and configuring the medical scanner 66 by another. In one embodiment, the image processor 62 is a control processor or other processor of a medical diagnostic imaging system, such as the medical scanner 66. The image processor 62 operates pursuant to stored instructions, hardware, and/or firmware to perform various acts described herein.

The image processor 62 is configured to train a machine learning architecture. Based on a user provided or other source of the network architecture and training data, the image processor 62 learns features for encoders, decoders, discriminators, or other network parts to train the network. The result of the training is a machine-learned model or models for 3D CT representation prediction with or without a machine-learned model for parameterization.

Alternatively or additionally, the image processor 62 is configured to apply one or more machine-learned models. For example, a generator is applied to surface data from the sensor. The machine-learned generative network is applied to surface information. Based on the previous training, the network generates a 3D CT representation in response to application of the surface data (e.g., depth information from measured depths) and in response to application of parameter locations, such as from the scanner 67 or from a machine-learned model. As another example, one machine-learned model may output a parameter probability map (e.g., heatmap), and another network may output the 3D CT representation based on input of the parameter probability map. Both networks may receive depth information for the outside of the patient as inputs. In one embodiment, the machine-learned model generates the CT volume in response to input of depth information and a segmentation and/or landmark locations. The segmentation and/or landmark location may be from output of another machine-learned model in response to input of surface data or from image processing from a scan of the patient.

In one embodiment, the machine-learned model was trained to generate a CT volume of a first type of anatomy and not a second type of anatomy despite the second type of anatomy being within the CT volume. For example, vessels or the cardiac system are represented while not including bone. In other embodiments, different channels are provided as output from the machine-learned model. The different channels output CT volumes for different types of anatomy, such as one channel outputting CT volume for cardiac representation and another outputting CT volume for bone representation.

The image processor 62 is configured to generate an image. The 3D CT representation is used for imaging, such as planar imaging a plane within the 3D CT volume, rendering a projection to 2D, or volume or surface rendering from 3D to a 2D image. Annotations or graphics, such as for the landmarks, may be added to the image.

The display 60 is a CRT, LCD, projector, plasma, printer, tablet, smart phone or other now known or later developed display device for displaying an image from the CT volume, such as an image volume rendered from a 3D CT representation. The display 60 displays a medical image estimated from the depth information.

The sensor measurements, fit shape model, surface data, network definition, features, machine-learned model or models, parameter maps, output 3D CT representation, and/or other information are stored in a non-transitory computer readable memory, such as the memory 64. The memory 64 is an external storage device, RAM, ROM, database, and/or a local memory (e.g., solid state drive or hard drive). The same or different non-transitory computer readable media may be used for the instructions and other data. The memory 64 may be implemented using a database management system (DBMS) and residing on a memory, such as a hard disk, RAM, or removable media. Alternatively, the memory 64 is internal to the processor 62 (e.g. cache).

The instructions for implementing the training or application processes, the methods, and/or the techniques discussed herein are provided on non-transitory computer-readable storage media or memories, such as a cache, buffer, RAM, removable media, hard drive or other computer readable storage media (e.g., the memory 64). Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU or system. Because some of the constituent system components and method steps depicted in the accompanying figures may be implemented in software, the actual connections between the system components (or the process steps) may differ depending upon the manner in which the present embodiments are programmed.

The medical scanner 66 is a medical diagnostic imaging system configured to scan a volume of a patient and generate anatomical information from the scan. The medical scanner 66 is a CT, MR, PET, SPECT, X-ray, or ultrasound scanner. The medical scanner 66 may be a same scanner or different scanner than the scanner 67.

The medical scanner 66 is configured to generate anatomical information. The configuration uses settings for one or more parameters, such as an X-ray source voltage, table position and/or range of movement, gantry position and/or range of movement, focus, field of view, scan density, detector thresholds, transmission sequence, image processing settings, filtering settings, or image generation settings.

Based on a 3D CT representation generated from the surface data rather than scanning by the medical scanner 66, one or more settings of the medical scanner 66 are set. The patient 69 is imaged by the medical scanner 66 using the settings. In alternative embodiments, scan data from the medical scanner 66 is used to determine the surface data, such as by fitting a statistical shape model that includes a skin mesh to the scan data.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for computed tomography (CT) prediction from surface data in a medical imaging system, the method comprising:
    capturing, with a sensor, an outer surface of a patient;
    determining a segmentation and/or a landmark location;
    generating, by an image processor, a first three-dimensional (3D) CT representation of the patient by a first machine-learned generative network in response to input of the surface data and the segmentation and/or landmark location to the first machine-learned generative network, the surface data being from an output of the sensor for the outer surface, the first machine-learned generative network comprising a generator architecture with an encoder and following decoder, where a beginning of the encoder has inputs for both (1) the segmentation and/or landmark location and for (2) the surface data and the decoder has an output for the first 3D CT representation, the segmentation different than the surface data; and
    displaying, by a display device, an image from the first 3D CT representation.

2. The method of claim 1 wherein capturing comprises capturing with the sensor being a depth sensor.

3. The method of claim 1 wherein capturing comprises capturing with the sensor being a camera where the surface data based on optical measurements.

4. The method of claim 1 wherein determining comprises determining the segmentation, and wherein generating comprises generating in response to the input of the surface data and the segmentation.

5. The method of claim 1 wherein determining comprises determining the segmentation and/or landmark location from scan data from a different medical imaging modality than CT.

6. The method of claim 1 wherein determining comprises determining the segmentation and the landmark location, and wherein generating comprises generating in response to the input of the surface data, the segmentation, and the landmark location.

7. The method of claim 1 wherein determining comprises determining with a second machine-learned generative network, the second machine-learned generative network outputting a segmentation map and/or landmark location map in response to input of the surface data and a second 3D CT representation of the patient, and wherein generating comprises generating by the first machine-learned generative network in response to input of the segmentation map as the segmentation and/or the landmark location map as the landmark location and input of the surface data.

8. The method of claim 7 further comprising forming the second 3D CT representation from an output of a third machine-learned generative network.

9. The method of claim 7 further comprising forming the second 3D CT representation from an output of the first machine-learned generative network.

10. The method of claim 9 wherein generating comprises iteratively using the first and second machine-learned generative networks.

11. The method of claim 1 wherein generating comprises generating the first 3D CT representation as a representation of first internal anatomy without second internal anatomy.

12. The method of claim 11 wherein generating further comprises generating a second 3D CT representation of the second internal anatomy without the first internal anatomy.

13. The method of claim 11 wherein generating comprises generating the first 3D CT representation as a voxel or mesh representation.

14. The method of claim 1 further comprising:
    configuring a medical scanner based on the first 3D CT representation; and
    imaging, by the medical scanner, the patient as configured based on the first 3D CT representation.

15. A method for computed tomography (CT) prediction from surface data in a medical imaging system, the method comprising:
    capturing, with a sensor, an outer surface of a patient;
    generating, by an image processor, a first three-dimensional (3D) CT representation by first and second machine-learned networks in response to input of the surface data to beginnings of both the first and second machine-learned networks, the surface data being from an output of the sensor for the outer surface, the first machine-learned network outputting a spatial segmentation based on the surface data, and the second machine-learned network outputting the first 3D CT representation based on the surface data and the spatial segmentation, the first and second machine-learned networks having been previously trained, the second machine-learned network comprising a generator having inputs for both the surface data and the spatial segmentation at the beginning of the generator; and
    displaying, by a display device, an image from the first 3D CT representation.

16. The method of claim 15 wherein the first machine-learned network is configured to output the spatial segmentation and a landmark map, and the second machine-learned network is configured to output based on the surface data, the spatial segmentation, and the landmark map.

17. The method of claim 15 wherein generating comprises generating the first 3D CT representation from one of one or more output channels, each output channel representing different ones of only muscle, only skeleton, only vessel, only organ, and only a tissue type.

* * * * *